United States Patent
Deaton

(10) Patent No.: US 7,015,344 B2
(45) Date of Patent: *Mar. 21, 2006

(54) SYNTHESIS OF ORGANOMETALLIC CYCLOMETALLATED GROUP VIIIB METAL COMPLEXES

(75) Inventor: Joseph C. Deaton, Rochester, NY (US)

(73) Assignee: Eastman Kodak Company, Rochester, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/879,412

(22) Filed: Jun. 29, 2004

(65) Prior Publication Data

US 2005/0288506 A1    Dec. 29, 2005

(51) Int. Cl.
*C07F 15/00*  (2006.01)
*H05B 33/14*  (2006.01)

(52) U.S. Cl. .................. 556/137; 546/10; 548/108; 428/690

(58) Field of Classification Search ............ 546/10; 556/137; 548/108; 428/690
See application file for complete search history.

(56) References Cited

U.S. PATENT DOCUMENTS

2002/0190250 A1    12/2002    Grushin et al. ............ 257/40

OTHER PUBLICATIONS

J. C. Deaton, et al., "Synthesis for Organometallic Cyclometallated Transition Metal Complexes", U.S. Appl. No. 10/729,263 (D-87223) filed Dec. 5, 2003.

*Primary Examiner*—Porfirio Nazario-Gonzalez
(74) *Attorney, Agent, or Firm*—Arthur E. Kluegel

(57) ABSTRACT

A process for forming an organometallic cyclometallated Group viiib metal complex comprises reacting a Group viiib metal compound with a heterocyclic compound capable of forming an organometallic cyclometallated complex in the presence of a solvent comprising an aromatic oxygen containing compound.

26 Claims, No Drawings

SYNTHESIS OF ORGANOMETALLIC CYCLOMETALLATED GROUP VIIIB METAL COMPLEXES

FIELD OF THE INVENTION

This invention relates to the field of organic synthesis and to a process for forming organometallic cyclometallated complexes of Group viiib metals comprising reacting a Group viiib metal compound with a heterocyclic compound capable of forming an organometallic cyclometallated complex in the presence of a solvent comprising an aromatic oxygen containing compound.

BACKGROUND OF THE INVENTION

Organometallic cyclometallated complexes of transition metals (e.g. rhodium, iridium, platinum) have become useful materials because of their photophysical and photochemical properties. One especially important application of these compounds are as phosphorescent dopants in Organic Light-Emitting Diodes (OLEDs) because of their strong emission from triplet excited states (M. A. Baldo, et al, *Appl. Phys. Letters*, 75, 4 (1999)). An important class of phosphorescent cyclometallated complexes contain ligands that are at least bidentate wherein one coordination site of the ligand to the metal is through an N atom that is doubly bonded to C or another N atom, usually as part of a heterocyclic ring, and wherein another coordination site of the ligand to the metal is through a C atom. As used herein, the term "organometallic cyclometallated complex" means that at least one of the coordination sites forming the cyclic unit binding the metal atom by at least one ligand must be a metal-carbon bond. The metal-carbon bond is formed in place of a hydrogen-carbon bond of the free ligand before it is complexed. The carbon atom forming the metal carbon bond is usually also doubly bonded to another carbon as in, for example, a phenyl ring or a thienyl ring or furanyl ring. Further the carbon atom forming the metal-carbon bond also is preferably positioned so as to form a five- or six-membered metallacycle including the coordinated N atom of the ligand. A tris-cyclometallated complex has three such ligands. Some examples of iridium(III) organometallic cyclometallated complexes are shown below.

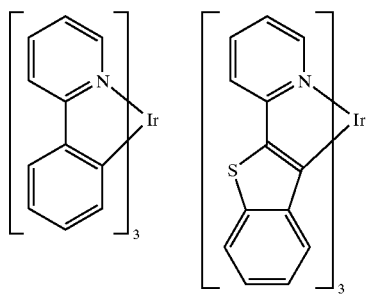

Further, there are two isomers, facial and meridional (fac and mer), possible for such complexes having three identical but unsymmetrical bidentate ligands as illustrated below. The facial isomers are typically more desirable in OLED applications because they usually have higher quantum yields.

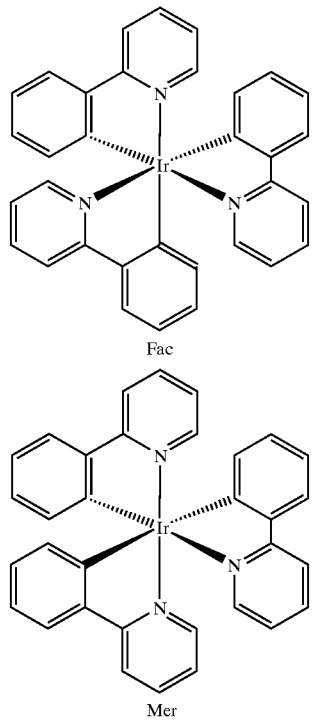

Fac

Mer

It is also possible that the organometallic cyclometallating ligands are not all the same. Further, the organometallic cyclometallated complex must have at least one cyclometallating ligand forming a metal-carbon bond, but may have additional types of ligands not forming metal-carbon bonds. A common type of the latter would be complexes of the form $L_2MX$ as described in WO 02/15645 A1. Here L is a cyclometallating ligand forming metal-carbon and metal-nitrogen bonds, while X is another monoanionic bidentate ligand that does not form metal carbon bonds, such as acetylacetonate.

The usefulness and importance of organometallic cyclometallated complexes of second- and third-row transition metals have necessitated synthetic methods for preparing them more efficiently. Chassot et al., *Inorg. Chem.*, 23, 4249–4253, (1984) have used lithiated ligands with platinum compounds that include leaving groups to form cyclometallated complexes of the ligands with platinum. Jolliet et al., *Inorg. Chem.*, 35, 4883–4888, (1996) also used lithiated ligands to form cyclometallated complexes of the ligands with platinum or palladium, and Lamansky and Thompson, in International Patent Application WO 00/57676, used the same procedure for cyclometallated platinum complexes. These procedures suffer from low yields, as well as the relative instability of and difficulty in handling lithiated organic materials.

Organometallic cyclometallated complexes may also be formed from direct reaction of the cyclometallating ligand, wherein the carbon-hydrogen is activated and replaced by the carbon-metal bond. For example, fac-tris(2-phenylpyridinato-N,$C^2$)iridium(III), or Ir(ppy)$_3$, was made by reaction of 2-phenylpyridine and tris(acetylacetonate) iridium (Ir(acac)$_3$) in glycerol solvent by K. Dedian et al, *Inorg. Chem.*, 30, 1685 (1991). Stössel and coworkers (WO 02060910) further optimized and improved this reaction, but still using the expensive Ir(acac)$_3$ starting material. By reacting less expensive halide complexes of Ir(III) such as iridium(III) chloride hydrate with 2-phenylpyridine in a solvent comprising a 3:1 mixture of 2-ethoxy-ethanol and water, Nonoyama obtained dimeric organometallic cyclometallated complexes such as tetrakis(2-phenyl-pyridinato-N,C$^{2'}$-) (di-$\mu$-chloro)di-iridium(III). (Note: Ir(ppy)$_3$ was later extracted as a side product in 10% yield from this reaction mixture, K. A. King, et al, *J. Am. Chem. Soc.*, 107, 1431 (1985).) This particular solvent and the related 2-methoxyethanol are not desirable for practical use due to adverse health effects. M. G. Colombo, et al *Inorg Chem.*, 33, 545 (1994), further reacted the above-cited di-iridium complex with a silver salt in neat 2-phenylpyridine to obtain Ir(ppy)$_3$ in 75% yield. Grushin et al U.S. 2002/0190250 used this process to make additional tris-cyclometalated complexes of Ir(III) having fluorine-substitutions on phenylpyridine and phenylquinoline cyclometallating ligands. But this process requires a large excess of a ligand since it is employed as the solvent, thereby either consuming valuable material or necessitating a process to recover excess ligand.

Lamasky et al., *Inorg. Chem.*, 40, 1704–1711, (2001) demonstrated yet another process for making tris-cyclometallated iridium complexes. First, a mixed ligand complex bis(7,8-benzoquinolinato-N,C$^{3'}$)iridium(III)(acetylacetonate) was made from tetrakis(7,8-benzoquinolinato-N,C$^{3'}$) (di-$\mu$-chloro)di-iridium(III). Then the bis(7,8-benzoquinolinato-N,C$^{3'}$)iridium(III)(acetylacetonate) was reacted with additional 7,8-benzoquinoline in refluxing glycerol to produce a mixture of isomers of the tris-cyclometallated complex, tris(7,8-benzoquinolinato-N,C$^{3'}$)iridium(III). Kamatani et al, U.S. 2003/0068526, have also employed this reaction type for additional cyclometallated iridium complexes. But this process often yields less-desireable meridional isomers or mixtures of the facial and meridonal isomers of the tris-cyclometallated complexes. Tamayo et al., *J. Am. Chem. Soc.*, 125, 7377–7387 (2003), have shown that reaction of dimeric organometallic cyclometallated complexes such as tetrakis(2-phenyl-pyridinato-N,C$^{2'}$-) (di-$\mu$-chloro)di-iridium(III) with sodium carbonate and additional cyclometallating ligand in glycerol can lead to formation of meridional isomers in many cases, while further reaction at higher temperatures results in formation of mostly facial isomer. However, this procedure is inconvenient for facial isomers as it necessitates finding exact conditions for the reaction of each ligand.

Copending commonly assigned U.S. Ser. No. 10/729,263 filed Dec. 5, 2003 describes a process for forming organometallic cyclometallated complexes of Ir(III) comprising the step of reacting a halide-containing complex of the metal with a silver salt and a heterocyclic organic ligand compound capable of forming an organometallic cyclometallated complex and in a solvent comprising an organic diol. However, this process fails in certain cases especially when the organometallic complex or intermediates have very low solubility in these solvents.

Despite the large number of investigations into the synthetic methodology for cyclometallated complexes, there remains a need for new methods that may provide better yields, higher purity, and control of desired isomers.

SUMMARY OF THE INVENTION

The invention provides a process for forming an organometallic cyclometallated Group viiib metal complex that comprises reacting a Group viiib metal compound with a heterocyclic compound capable of forming an organometallic cyclometallated complex in the presence of a solvent comprising an aromatic oxygen containing compound. Such a process may improve the yields, purity and/or desired isomer control.

DETAILED DESCRIPTION OF THE INVENTION

The invention is summarized above. The process comprises reacting a Group viiib metal compound, such as Pt, Ir, Rh, Pd, Os, or Ru, with a heterocyclic compound capable of forming an organometallic cyclometallated complex in the presence of a solvent comprising an aromatic oxygen containing compound to form an organometallic cyclometallated Group viiib metal complex.

In one embodiment, Group viiib metal compound is six-coordinate and comprises materials represented by the Formula (1).

$$MY_6 \qquad (1)$$

In Formula (1), M represents a Group viiib metal and desirably M represents iridium. Each Y represents an independently selected ligand group, wherein each Y may be the same or different. Illustrative examples of Y are Cl, Br, and H$_2$O. Compounds of Formula (1) may be negatively charged, in which case a counterion, such as sodium or potassium, is necessary to balance the charge. In one suitable embodiment, at least one Y of Formula (1) represents a halogen. Examples of Formula (1) compounds are iridium (III) chloride hydrate, iridium(III) bromide hydrate, tripotassium hexachloroiridate(III) and tripotassium hexachloroiridate(III), rhodium(III) chloride hydrate, rhodium(III) bromide hydrate. Anhydrous metal halides such as iridium (III) chloride, iridium(III) bromide, and rhodium(III) chloride may also be used in place of compounds of Formula (1).

In another embodiment, the Group viiib metal compound includes those represented by the Formula (2).

$$(L)_2M(\mu\text{-}X)_2M(L)_2 \qquad (2)$$

In Formula (2) each L represents an independently selected bidentate cyclometallating ligand, $\mu$-X represents a bridging halide, such as Cl or Br. M represents a Group viiib metal, such as iridium.

As described previously, a bidentate cyclometallating ligand is a ligand wherein one coordination site of the ligand to the metal is through an N atom that is doubly bonded to C or another N atom, usually as part of a heterocyclic ring, and wherein another coordination site of the ligand to the metal is through a C atom. Illustrative examples of bidentate cyclometallating ligands are listed below.

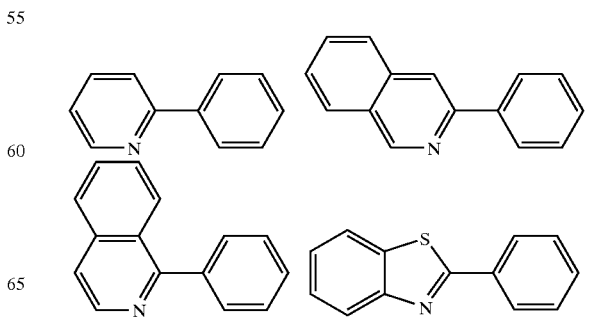

-continued

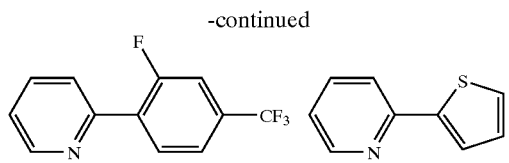

In another aspect of the invention, Group viiib metal compound can be represented by the Formula (3)

$$[(L)_2M(L^1)_2]+X^- \quad (3)$$

In Formula (3), M represents Group viiib metal compound, such as Ir or Rh; in one desirable embodiment M represents Ir. X⁻ represents an anionic counterion, such a tetrafluoroborate or hexafluorophosphonate. Each L represents an independently selected bidentate cyclometallating ligand and each L may be the same or different. In one embodiment, L represents the same ligand in each case.

Each $L^1$ represents an independently selected monodentate ligand, which may be the same or different. In one embodiment the monodentate ligands are the same. Monodentate ligands form only one bond to the metal, for example a thiocyanate ion is a mondentate ligand. In one embodiment the monodentate ligand is not charged. For example, suitable neutral monodentate ligands include nitriles, such as acetonitrile and propionitrile, sulfoxides, such as dimethylsulfoxide, and amides such as dimethylformamide, and water.

In yet another aspect of invention, the Group viiib metal compound includes those represented by Formula (4).

$$L_2MX \quad (4)$$

In Formula (4), each $L_2$ represents an independently selected bidentate organometallic cyclometallating ligand, while X represents a monoanionic bidentate ligand that does not form metal carbon bonds, such as acetylacetonate. Complexes of Formula (4) may be prepared as described in WO 02/15645.

The process comprises reacting a Group viiib metal compound with a heterocyclic compound capable of forming an organometallic cyclometallated complex. In one desirable embodiment the heterocyclic compound is a bidentate cyclometallating ligand corresponding to L, which has already been described.

The process further comprises reacting the materials in the presence of a solvent comprising an aromatic oxygen containing compound. Aromatic oxygen containing compounds are solvents that provide a suitable medium for the organometallic cyclometallation reactions, but are less viscous than, for example, glycerol, and therefore it is easier to perform such operations as transfer and filtering. These solvents are often capable of dissolving the reactants or intermediates more readily than other solvents used for organometallic cyclometallation reactions, such as glycerol, diols, or 2-ethoxyethanol and the like. Solvents useful in the invention also provide high product yields and high isomeric purity. Examples of useful solvents include, but are not limited to organic esters such as phenyl acetate, methyl benzoate, phenyl benzoate, ethyl benzoate, phenyl propionate, phenyl, 3-hydroxypropionate, furfuryl benzoate, furfuryl acetate, phenyl 2-furoate and organic ethers, for example, 2-phenoxyethanol, 2-phenoxypropanol, 2-(furan-2-oxy)ethanol.

In one embodiment, the aromatic oxygen containing compound is represented by Formula (1a), (1b), or 1(c).

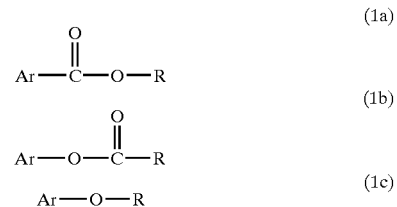

In Formulas (1a)–(1c), Ar represents an aromatic group, for example a phenyl group or a furanyl group, R represents a substituent, such as a methyl group, or a phenyl group. In one suitable embodiment, Ar represents an aryl group, such as a phenyl group and R represents an aliphatic group. Examples of suitable R groups include aliphatic hydrocarbon groups of 1 to 10 carbons and aliphatic alcohol groups.

The reaction mixtures formed in the process may be conveniently heated to the reflux temperature of the solvent, or may be held in a constant temperature bath. A suitable temperature range for the reactions is 80 to 250° C. but more commonly is 140 to 220° C.

In one aspect of the invention, the process comprises reacting a compound of Formula (1), wherein at least one Y represents a halide, or a compound of Formula (2) with a heterocyclic compound capable of forming an organometallic cyclometallated complex (for example a compound represented by L), in the presence of a solvent comprising an aromatic oxygen containing compound and in the presence of a silver salt to form a tris-cyclometallated Group viiib metal complex of Formula (5). Compounds of Formula (3) or (4) may be used in an analogous manner to form compounds of formula (5) except that no silver salt is required.

$$M(L)_3 \quad (5)$$

In Formula (5), as described previously, M represents a Group viiib metal such as Ir or Rh and each L represents an independently selected bidentate cyclometallating ligands and each L may be the same or different.

Compounds of Formula (2), Formula (3), Formula (4), L, and suitable solvents have been described previously. Silver salts useful in the invention include soluble salts with an anion such as tetrafluoroborate, trifluoroacetate, or trifluoromethanesulfonate. It is also possible to use other metal ion salts in the process of the invention if the metal ions form insoluble compounds with halide ions. Examples would be salts of thallium. However, thallium salts are not suitable for manufacturing processes due to the toxic effects of thallium. The reaction vessel may be initially charged with all of the silver salt needed for the reaction, or the silver salt may be added slowly as a solution in additional reaction solvent during the course of the reaction to avoid high concentrations of silver that may lead to reduction of silver.

In another embodiment of this invention, the process includes reacting a metal compound of Formula (1) with a heterocyclic compound such as those represented by L as described previously, in the presence of a solvent comprising an aromatic oxygen containing compound to form a metal compound of Formula (2). The compound of Formula (2) is then further reacted in the presence of a silver salt, in a second reaction step to form complexes of Formula (5), wherein the two reaction steps are conducted sequentially in the same reaction vessel. In this case it is not necessary to isolate the complex of Formula (2). The silver salt may all be added in the initial set-up of the reaction vessel, or may be added to the reaction vessel after the first reaction step when the formation of Formula (2) is complete.

The option of performing both steps in the same reaction vessel provides convenience and simplification, as long as enough silver salt is added to consume all the halide from the starting material.

The process is carried out for a sufficient length of time to produce substantial amounts of the cyclometallated complex. Suitable reaction times can be determined by monitoring the reaction. For example, by removing aliquots of the reaction mixture periodically and by using thin-layer-chromatography (TLC) or high-performance-liquid chromatography (HPLC) analysis one can determine the amount of reactants present, and one can determine the amount of product formed. In this manner the progress of the reaction can be monitored. Typically the reaction times are 1 to 24 h, but may be shorter or longer.

Suitably the cyclometallated complex product can be isolated and purified if necessary. Purification can be done by well-known methods such as sublimation, crystallization or column chromatography.

Embodiments of the invention can provide more convenient methods employing less expensive starting materials and solvents that are applicable to a wide range of cyclometallating ligands.

Illustrative examples of tris-cyclometallated compounds of Formula (5) are listed below.

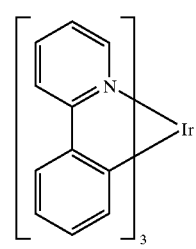

5a

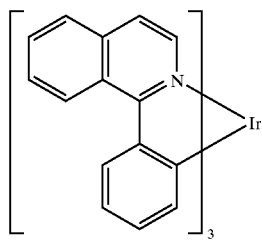

5b

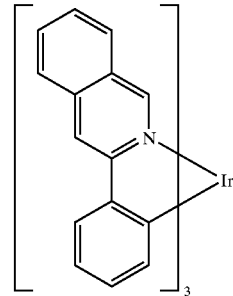

5c

-continued

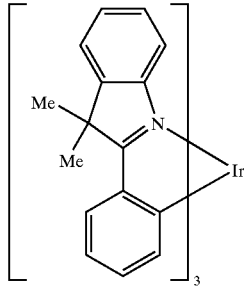

5d

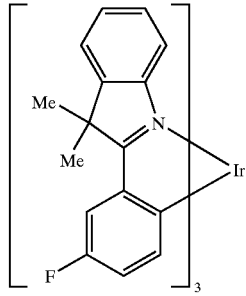

5e

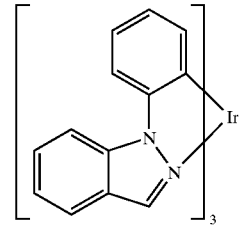

5f

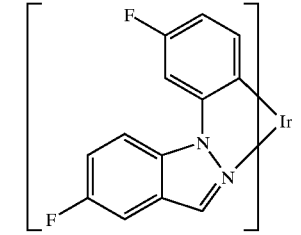

5g

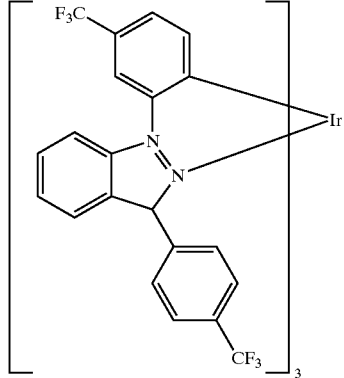

5h

-continued

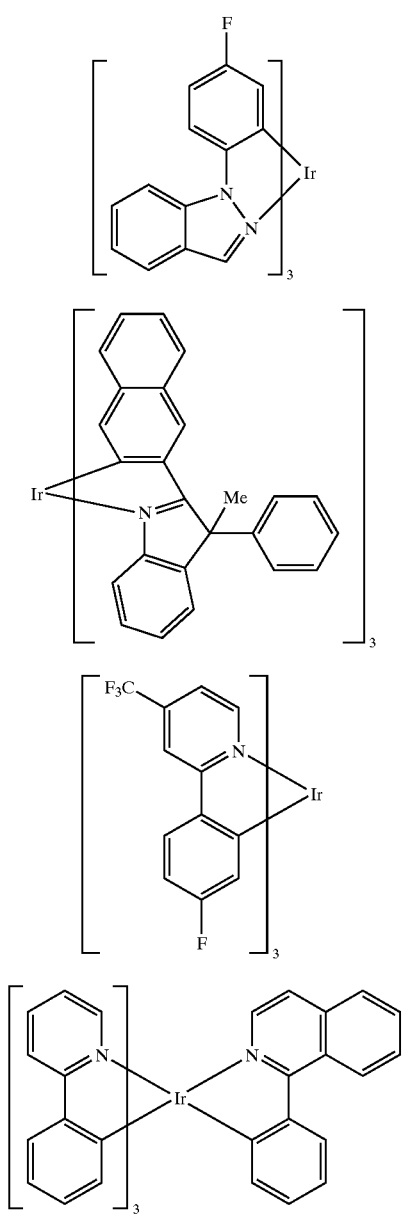

Embodiments of the invention may provide convenient methods of synthesis, employ relatively inexpensive starting materials and solvents, and be applicable to a wide range of cyclometallating ligands. Embodiments may also provide higher yields of tris-cyclometallated complexes having fewer impurities.

The invention and its advantages can be better appreciated by the following examples.

EXAMPLE 1

Preparation of fac-tris(2-phenylpyridinato-N,$C^{2'}$) iridium(III) in phenyl acetate Tetrakis(2-phenylpyridinato-N,$C^{2'}$)($\mu$-dibromo)diiridium (III) (0.68 g, 0.59 mmol), 2-phenylpyridine (0.42 mL) and silver trifluoroacetate (0.36 g.) were placed in a 100-mL round-bottomed flask with 30 mL of phenyl acetate and the mixture was freeze-thaw degassed, and then refluxed for 3 h under nitrogen atmosphere. After cooling, a yellow precipitate was collected by filtration, washed with ethanol, and dried under vacuum to afford 0.638 g of product. The product was sublimed in a tube furnace with nitrogen entrainment gas (295–300° C., 0.7 Torr) to yield 0.413 g (56% yield) of fac-tris(2-phenylpyridinato-N,C $^{2'}$)iridium (III). Analysis by high-performance-liquid-chromatography and mass spectroscopy confirmed the structure.

EXAMPLE 2

Preparation of fac-tris(3-phenylquinolinato-N,$C^{2'}$) iridium(III) in phenyl acetate Tetrakis(3-phenyl-quinolinato-N,$C^{2'}$)($\mu$-dibromo)diiridium(III) (0.46 g, 0.34 mmol) and 3-phenylisoquinoline (0.35 g.) and silver trifluoroacetate (0.21 g) were placed in a 50 mL round-bottomed flask with 20 mL of phenyl acetate. The mixture was freeze-thaw degassed, and then refluxed for 4 h under nitrogen atmosphere. After cooling, an orange precipitate was collected by filtration and dried to afford 0.64 g of orange product. Analysis by high-performance-liquid-chromatography and mass spectrometry indicated that the product was fac-tris(3-phenyl-isoquinolinato-N,$C^{2'}$) iridium(III). The crude product also likely contained silver metal, and could be purified by sublimation or by Soxhlet extraction in methylene chloride.

EXAMPLE 3

Preparation of fac-tris(2-phenylpyridinato-N,$C^{2'}$) iridium(III) in methyl benzoate Tetrakis(2-phenylpyridine-N,$C^{2'}$)($\mu$-dibromo)diiridium (III) (0.38 g, 0.33 mmol) and silver trifluoroacetate (0.206 g.) were placed in a 50-mL round-bottomed flask with 20 mL of methyl benzoate and 2-phenylpyridine (0.26 g) was added and the mixture was freeze-thaw degassed, and then refluxed for 3 h under nitrogen atmosphere. After cooling, a yellow precipitate was collected by filtration. The yellow solid was dissolved in approximately 50 mL of methylene chloride and insoluble material was filtered. The filtrate was concentrated under vacuum until a yellow precipitate formed and then methanol was added to further precipitate the product. The yellow solid was collected by filtration and dried to afford 0.28 g of fac-tris(2-phenylpyridinato-N,$C^{2'}$)iridium(III) which was confirmed by mass spectrometry and HPLC analysis. The crude product also likely contained silver metal, and could be purified by sublimation or by Soxhlet extraction in methylene chloride.

The above examples illustrate that the process provides a convenient method to prepare organometallic cyclometallated Group viiib metal complexes.

The entire contents of the patents and other publications referred to in this specification are incorporated herein by reference. The invention has been described in detail with particular reference to certain preferred embodiments thereof, but it will be understood that variations and modifications can be effected within the spirit and scope of the invention.

What is claimed is:

1. A process for forming an organometallic cyclometallated Group viiib metal complex comprising reacting a Group viiib metal compound with a heterocyclic compound capable of forming an organometallic cyclometallated complex in the presence of a solvent comprising an aromatic oxygen containing compound.

2. A process according to claim 1 wherein the metal is Pt, Ir, Rh, Pd, Os, or Ru.

3. A process according to claim 1 wherein the metal is Ir(III).

4. A process according to claim 1 wherein aromatic oxygen containing compound is an aromatic ester compound.

5. A process according to claim 1 wherein the aromatic oxygen containing compound is represented by Formula (1a) or Formula (1b):

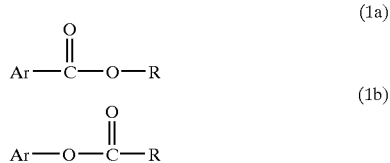

wherein:
Ar represents an aromatic group; and
R represents a substituent.

6. A process according to claim 5 wherein Ar represents a carbocyclic group and R represents an aliphatic group.

7. A process according to claim 1 wherein aromatic oxygen containing compound is an aromatic ether compound.

8. A process according to claim 1 wherein the aromatic oxygen containing compound is represented by Formula (1c):

wherein:
Ar represents an aromatic group; and
R represents a substituent.

9. A process according to claim 8 wherein Ar represents a carbocyclic group and R represents an aliphatic group.

10. A process according to claim 1 wherein aromatic oxygen containing compound is phenyl acetate or methyl benzoate.

11. A process according to claim 1 wherein the Group viiib metal compound comprises a material represented by the formula $M(Y)_6$, wherein M represents a Group viiib metal; and each Y represents an independently selected ligand group.

12. A process according to claim 11 wherein at least one Y represents a halide.

13. A process according to claim 1 wherein the Group viiib metal compound is represented by Formula (2):

wherein:
each L represents an independently selected bidentate cyclometallating ligand;
Each μ-X represents a bridging halide; and
M represents a Group viiib metal.

14. A process according to claim 1 wherein the metal compound is represented by Formula (3):

wherein:
M represents Ir or Rh;
$X^-$ represents an anionic counterion;
each L represents an independently selected bidentate cyclometallating ligand; and
each $L^1$ represents an independently selected monodentate ligand.

15. A process according to claim 1 wherein the heterocyclic compound comprises a 2-phenylpyridine group.

16. A process according to claim 1 wherein the heterocyclic compound comprise a 3-phenylisoquinoline group.

17. A process according to claim 1 wherein the heterocyclic compound comprise a 1-phenylisoquinoline group.

18. A process according to claim 1 wherein a compound comprising an organometallic bis-cyclometallated complex is formed.

19. A process according to claim 1 wherein a compound comprising an organometallic tris-cyclometallated complex is formed.

20. A process according to claim 1 wherein the cyclometallated metal complex formed comprises a 2-phenylpyridine group.

21. A process according to claim 1 wherein the cyclometallated metal complex formed comprises a 3-phenylisoquinoline group.

22. A process according to claim 1 wherein the cyclometallated metal complex formed comprises a 1 phenylisoquinoline group.

23. A process according to claim 1 wherein organometallic cyclometallated Group viiib metal complex formed is represented by Formula (2):

wherein:
each L represents an independently selected bidentate cyclometallating ligand;
Each μ-X represents a bridging halide; and
M represents a Group viiib metal.

24. A process according to claim 1 wherein organometallic cyclometallated Group viiib metal complex formed is represented by Formula (5):

wherein
M represents a Group viiib metal; and
each L represents an independently selected bidentate cyclometallating ligand.

25. A process according to claim 1 comprising two steps, wherein:
a) in the first step a Group viiib metal compound of Formula (1) is reacted with a heterocyclic compound capable of forming an organometallic cyclometallated complex in the presence of a solvent comprising an aromatic oxygen containing compound to form a compound of Formula (2), and
b) in the second step the compound of Formula (2) is further reacted with a heterocyclic compound capable of forming an organometallic cyclometallated complex in the presence of a solvent comprising an aromatic oxygen containing compound to form a compound of Formula (5), wherein the formulas are

in which
M represents a Group viiib metal;
each Y represents a ligand group;
each L represents an independently selected bidentate cyclometallating ligand group; and
Each μ-X represents a bridging halide.

26. A process according to claim 25 wherein both steps are performed in the same reaction vessel.

* * * * *